(12) United States Patent
Popitz et al.

(10) Patent No.: US 10,888,183 B2
(45) Date of Patent: Jan. 12, 2021

(54) METHOD, SYSTEM, AND APPARATUS FOR FACILITATING POSITIONING A PERSON IN SUPINE SNIFF POSITION

(71) Applicant: Popitz, LLC, Wellesley, MA (US)

(72) Inventors: Michael D. Popitz, Marion, MA (US); Jesse S. Drake, Westborough, MA (US); Justin McCarthy, Boxborough, MA (US)

(73) Assignee: Popitz, LLC, Wellesley, MA (US)

( * ) Notice: Subject to any disclaimer, the term of this patent is extended or adjusted under 35 U.S.C. 154(b) by 0 days.

(21) Appl. No.: 16/689,081

(22) Filed: Nov. 20, 2019

(65) Prior Publication Data

US 2020/0154914 A1    May 21, 2020

Related U.S. Application Data

(60) Provisional application No. 62/861,859, filed on Jun. 14, 2019, provisional application No. 62/836,558, filed on Apr. 19, 2019, provisional application No. 62/824,203, filed on Mar. 26, 2019, provisional application No. 62/772,492, filed on Nov. 28, 2018, provisional application No. 62/769,869, filed on Nov. 20, 2018.

(51) Int. Cl.
*A47G 9/10* (2006.01)
*A61G 7/07* (2006.01)

(52) U.S. Cl.
CPC ........... *A47G 9/1081* (2013.01); *A47G 9/109* (2013.01); *A61G 7/07* (2013.01); *A61G 7/072* (2013.01); *A47G 2009/1018* (2013.01); *A61G 2200/322* (2013.01); *A61G 2200/327* (2013.01)

(58) Field of Classification Search
CPC ................................ A47G 9/1081; A47G 9/10
USPC ....................................................... 5/636, 640
See application file for complete search history.

(56) References Cited

U.S. PATENT DOCUMENTS

| 2,700,779 A | 2/1955 | Tolkowsky |
| 3,369,548 A | 2/1968 | Moore |
| 4,118,813 A | 10/1978 | Armstrong |

(Continued)

FOREIGN PATENT DOCUMENTS

| EP | 1488766 A1 | 12/2004 |
| EP | 2201921 A2 | 6/2010 |

(Continued)

OTHER PUBLICATIONS

International Invitation to Pay Additional fees, PCT/US2019/062309, dated Jan. 17, 2020, 12 pages.

(Continued)

*Primary Examiner* — Frederick C Conley
(74) *Attorney, Agent, or Firm* — Nelson Mullins Riley & Scarborough LLP; Thomas J. Engellenner; Reza Mollaaghababa

(57) ABSTRACT

Embodiments of an apparatus for supporting the neck and head of a user for airway management are described. The apparatus can include a base support section, which can rest on a supporting surface, a front side, two opposing sides and a back side with the base support section being dimensioned between about 25-26 inches in width, between about 16-17 inches in depth and about 6 inches in height with a separate and removable and replaceable head/neck support section.

10 Claims, 3 Drawing Sheets

(56) References Cited

U.S. PATENT DOCUMENTS

| | | |
|---|---|---|
| 4,218,792 A | 8/1980 | Kogan |
| 4,424,599 A | 1/1984 | Hannouche |
| 4,494,261 A | 1/1985 | Morrow |
| 4,550,458 A | 11/1985 | Fiore |
| 4,768,246 A * | 9/1988 | Summer ............... A47G 9/10 5/640 |
| 4,850,067 A | 7/1989 | Latorre |
| 4,918,774 A | 4/1990 | Popitz |
| 5,018,231 A | 5/1991 | Wang |
| 5,048,136 A | 9/1991 | Popitz |
| 5,457,832 A | 10/1995 | Tatum |
| 5,848,448 A | 12/1998 | Boyd |
| 6,003,177 A | 12/1999 | Ferris |
| 6,006,380 A | 12/1999 | Sramek |
| 6,381,784 B1 | 5/2002 | Davis et al. |
| 6,401,279 B1 | 6/2002 | Vaughn |
| 6,408,468 B1 | 6/2002 | Comfort |
| 6,446,288 B1 * | 9/2002 | Pi ............................ A47G 9/10 5/636 |
| 6,622,325 B1 | 9/2003 | Garza |
| 6,671,907 B1 | 1/2004 | Zuberi |
| 6,751,818 B2 | 6/2004 | Troop |
| 6,915,539 B2 | 7/2005 | Rathbun |
| 6,935,340 B2 | 8/2005 | Saied |
| 7,020,919 B2 | 4/2006 | Inaba |
| 7,077,141 B2 | 7/2006 | Troop |
| 7,082,633 B1 | 8/2006 | Maarbjerg |
| 7,089,615 B1 | 8/2006 | Parimuha |
| 7,100,227 B2 | 9/2006 | Frisbee |
| 7,127,758 B2 | 10/2006 | Gabbay |
| 7,127,759 B2 | 10/2006 | Koops |
| 7,213,280 B2 | 5/2007 | Lavin et al. |
| 7,350,250 B2 | 4/2008 | Froelich |
| 7,383,599 B2 | 6/2008 | Gabbay |
| 7,406,732 B2 | 8/2008 | Ramaiah |
| 7,467,431 B2 | 12/2008 | Weedling et al. |
| 7,546,651 B2 | 6/2009 | Groteke et al. |
| 7,594,288 B1 | 9/2009 | Holliday et al. |
| 7,676,870 B2 | 3/2010 | Chen |
| 7,681,262 B2 | 3/2010 | Weedling et al. |
| 7,716,763 B2 | 5/2010 | Nissen et al. |
| 7,908,591 B1 | 3/2011 | Nell et al. |
| 7,908,691 B2 | 3/2011 | Small |
| 7,926,134 B2 | 4/2011 | Carlos |
| 8,001,636 B2 | 8/2011 | Nissen et al. |
| 8,065,766 B1 | 11/2011 | Fierro |
| 8,069,515 B1 | 12/2011 | Tingey |
| 8,118,030 B1 | 2/2012 | Bugeja |
| 8,161,588 B1 | 4/2012 | Anson |
| 8,176,586 B2 | 5/2012 | Berke et al. |
| 8,176,921 B2 | 5/2012 | Bazargani |
| 8,234,732 B2 | 8/2012 | Bacon |
| D668,092 S | 10/2012 | Davis et al. |
| 8,291,534 B2 | 10/2012 | Karlson |
| 8,316,489 B1 | 11/2012 | Leal |
| 8,429,775 B2 | 4/2013 | North |
| 8,459,264 B2 | 6/2013 | Tweardy |
| 8,512,370 B2 | 8/2013 | Sorensen |
| 8,566,985 B2 | 10/2013 | Kim |
| 8,650,684 B1 | 2/2014 | Mackinnon |
| 8,671,481 B2 | 3/2014 | Franklin |
| 8,677,531 B2 | 3/2014 | Popitz |
| 8,769,744 B1 | 7/2014 | Brown |
| 8,806,685 B2 | 8/2014 | Karlson |
| 8,813,282 B2 | 8/2014 | Roban |
| 8,973,190 B2 | 3/2015 | Oh et al. |
| 8,997,285 B2 | 4/2015 | Moore |
| 9,220,345 B2 | 12/2015 | Davis et al. |
| 9,241,586 B1 | 1/2016 | Brown |
| 9,265,681 B1 | 2/2016 | Bell |
| 9,289,082 B1 | 3/2016 | White et al. |
| 9,357,864 B2 | 6/2016 | Campagna |
| 9,510,986 B2 | 12/2016 | Nesley |
| 9,572,739 B1 | 2/2017 | Bell |
| 9,707,152 B2 | 7/2017 | Lurie et al. |
| 9,750,661 B2 | 9/2017 | Lurie et al. |
| 9,801,782 B2 | 10/2017 | Lurie et al. |
| 9,808,370 B1 | 11/2017 | Reser et al. |
| D851,424 S | 6/2019 | Santjer |
| D867,021 S | 11/2019 | Yang |
| 2002/0059680 A1 | 5/2002 | Mahoney et al. |
| 2004/0010288 A1 | 1/2004 | Ghaly |
| 2004/0139549 A1 | 7/2004 | Mohrekesh et al. |
| 2005/0081866 A1 | 4/2005 | Saied |
| 2005/0102756 A1 | 5/2005 | Martin |
| 2006/0260055 A1 | 11/2006 | Frisbee |
| 2007/0006382 A1 | 1/2007 | Guez |
| 2007/0011812 A1 | 1/2007 | Drucker |
| 2007/0144538 A1 | 6/2007 | Tweardy |
| 2007/0181122 A1 | 8/2007 | Mulier |
| 2007/0294829 A1 | 12/2007 | Callahan et al. |
| 2008/0086818 A1 | 4/2008 | Sramek et al. |
| 2008/0092908 A1 | 4/2008 | Costa |
| 2008/0134437 A1 | 6/2008 | Small |
| 2008/0163428 A1 | 7/2008 | Groteke et al. |
| 2008/0222813 A1 | 9/2008 | Aikman |
| 2008/0282473 A1 | 11/2008 | Ramaiah |
| 2009/0038077 A1 | 2/2009 | Han et al. |
| 2009/0139031 A1 | 6/2009 | Davis et al. |
| 2009/0211031 A1 | 8/2009 | Kloes et al. |
| 2009/0241967 A1 | 10/2009 | Orencel |
| 2010/0125955 A1 | 5/2010 | Mendez et al. |
| 2010/0229875 A1 | 9/2010 | Davis |
| 2010/0281616 A1 | 11/2010 | Karlson |
| 2011/0056502 A1 | 3/2011 | Davis et al. |
| 2011/0094033 A1 | 4/2011 | Lee |
| 2011/0162146 A1 | 7/2011 | Frydman |
| 2011/0271964 A1 | 11/2011 | Zhang |
| 2012/0060846 A1 | 3/2012 | Leoniak et al. |
| 2012/0073057 A1 | 3/2012 | Sramek |
| 2012/0079660 A1 | 4/2012 | Chen |
| 2013/0091632 A1 | 4/2013 | Roban |
| 2013/0245395 A1 | 9/2013 | Bidarian Moniri |
| 2014/0096777 A1 | 4/2014 | Derner |
| 2014/0208515 A1 | 7/2014 | Sramek |
| 2014/0296747 A1 | 10/2014 | Herrnsdorf |
| 2015/0128348 A1 | 5/2015 | Gottlieb |
| 2015/0208812 A1 | 7/2015 | Fenton |
| 2015/0265075 A1 | 9/2015 | Liu et al. |
| 2016/0106238 A1 | 4/2016 | Vargas |
| 2016/0151222 A1 | 6/2016 | Pedro et al. |
| 2016/0354265 A1 | 12/2016 | Usoltseff |
| 2017/0027344 A1 | 2/2017 | Herrnsdorf et al. |
| 2017/0239076 A1 | 8/2017 | Stanton |
| 2017/0245656 A1 | 8/2017 | Ribble et al. |
| 2017/0246066 A1 | 8/2017 | Reilly et al. |
| 2017/0258627 A1 | 9/2017 | Cuzzetto |
| 2017/0326017 A1 | 11/2017 | Marinkovic |
| 2018/0064573 A1 | 3/2018 | Mello et al. |
| 2018/0078061 A1 | 3/2018 | Randall |
| 2018/0220818 A1 | 8/2018 | Doughty |
| 2018/0256387 A1 | 9/2018 | Anderson |
| 2019/0069698 A1 | 3/2019 | Lin |

FOREIGN PATENT DOCUMENTS

| | | |
|---|---|---|
| WO | 2001032112 A1 | 5/2001 |
| WO | 2005018512 A1 | 3/2005 |
| WO | 2008146429 A1 | 12/2008 |
| WO | 2009063299 A2 | 5/2009 |
| WO | 2010019237 A2 | 2/2010 |
| WO | 2010052532 A1 | 5/2010 |
| WO | 2010071899 A1 | 6/2010 |
| WO | 2010082758 A2 | 7/2010 |
| WO | 2014011123 A1 | 1/2014 |
| WO | 2014021518 A1 | 2/2014 |
| WO | 2014181020 A1 | 11/2014 |
| WO | 2015119403 A1 | 8/2015 |
| WO | 2015161146 A1 | 10/2015 |
| WO | 2016034923 A1 | 3/2016 |
| WO | 2016075464 A1 | 5/2016 |

(56) References Cited

FOREIGN PATENT DOCUMENTS

| | | |
|---|---|---|
| WO | 2017166826 A1 | 10/2017 |
| WO | 2018232549 A1 | 12/2018 |

OTHER PUBLICATIONS

International Invitation to Pay Additional fees, PCT/US2019/062307, dated Jan. 17, 2020, 12 pages.
International Invitation to Pay Additional fees, PCT/US2019/062310, dated Jan. 21, 2020, 12 pages.
U.S. Appl. No. 16/689,088, filed Nov. 20, 2019, Michael D. Popitz, et al.
U.S. Appl. No. 16/689,083, filed Nov. 20, 2019, Michael D. Popitz, et al.
U.S. Appl. No. 29/713,974, filed Nov. 20, 2019, Michael D. Popitz, et al.
U.S. Appl. No. 29/713,975, filed Nov. 20, 2019, Michael D. Popitz, et al.

* cited by examiner

METHOD, SYSTEM, AND APPARATUS FOR FACILITATING POSITIONING A PERSON IN SUPINE SNIFF POSITION

PRIOR APPLICATIONS

This Application claims priority to and the benefit of U.S. Provisional Application No. 62/861,859 filed on Jun. 14, 2019, U.S. Provisional Application No. 62/836,558 filed on Apr. 19, 2019, U.S. Provisional Application No. 62/824,203 filed on Mar. 26, 2019, U.S. Provisional Application No. 62/772,492 filed on Nov. 28, 2018, and U.S. Provisional Application No. 62/769,869 filed on Nov. 20, 2018. The entire teachings of these earlier applications are incorporated herein by reference.

TECHNICAL FIELD

The present disclosure relates to a head-positioning apparatus (herein also referred to as a pillow) that provides adjustable sizing for a variety of user head and neck sizes for supporting the user's head and neck and reducing the risk of acid reflux while sleeping in the supine position, and aligning the user's oropharyngeal, laryngeal, and tracheal axes of the human head and neck for airway management while in the supine position. The support pillow incorporates a ramp which reduces the risk of acid reflux occurring and a removable head and neck section which are dimensioned to align the airway axes when the head and neck are positioned thereupon in order to manage air flow, reduce snoring and sleep apnea.

BACKGROUND

Obstructive breathing may occur during sleep, or sedation, most commonly in the supine position due to the effects of gravity on the tongue. To help alleviate this issue, pillows have been developed to reduce airway obstruction in the supine position, by designing the tracheal axes to place the patient into the "sniff" position, which has been determined to be the most effective positional method for improving the patency of the airway and therefore enhancing the volume and smoothness of the flow of air or oxygen into the patient and the flow of carbon dioxide out.

However, there are shortcomings conventional pillows. The current art for sniff pillows uses in its construction a single piece monolith block, and since users' morphologies (head and neck sizes) vary greatly, it follows that many differing sized pillows of this monolithic design must be offered, and inventoried, adding to the cost and complexity of manufacturing and distribution of such an apparatus. In addition, the current pillows are not configured to reduce the incidence of acid reflux that may occur in some users whilst sleeping in the supine position.

Accordingly, there is a need for enhanced pillows that can address these shortcomings.

SUMMARY

Embodiments disclosed herein address and overcome one or more of the above shortcomings and drawbacks, by providing methods, systems, and apparatuses that maintain airway flow and help eliminate acid reflux that some users experience while in the supine position, while reducing the complexity and cost involved by properly sizing the pillow to varying user morphologies.

An apparatus for supporting the neck and head of a user for airway management can include a base support section, which can rest on a supporting surface, a front side, two opposing sides and a back side with the base support section being dimensioned between about 25-26 inches in width, between about 16-17 inches in depth and about 6 inches in height with a separate and removable and replaceable head/neck support section.

For example, the apparatus the base support section can have a receptacle area cut into the top surface of the base support section ("receptacle cutout") for receiving the separate neck/head support section.

The front side of the base support base section can have a shoulder receiving area with a ramped surface sloping upwards, and away from the supporting surface of the front edge of the pillow at an angle of at least 15° and no more than 45° relative to said support surface, and towards the receptacle cutout on the top of the base support section; the receptacle cutout being of sufficient depth to receive, and mate snugly with, the separate head/neck support section. The back side of the base support section can also have a surface that slopes upwards away from the support surface underneath the apparatus and upwards towards receptacle cutout. In other words, when the pillow is resting on a support surface, the ramp can form an angle of at least about 15° and no more than about 45° relative to the support surface.

In some embodiments, the separate head/neck support section can be configured to fit snugly in the base support section. In other embodiments, the separate head/neck support section fits loosely in the base support section. Fitting snugly as used herein means that a distance or clearance between the two opposing surfaces is equal to or less than $5/100^{th}$ of an inch, fitting loosely is defined as the distance between the opposing surfaces being greater than $5/100$ of an inch but less than $1/10$ of an inch.

Additionally or alternatively, the separate head/neck support can be generally oval or round in shape having a depth ranging between about ½ inches and about 6 inches and a maximum width of about 14 inches. For example, the head/neck support can be rectilinear in shape but conforming to the same dimensions.

Further, the separate head/neck support section can be configured to fit snugly into the base support section. Additionally or alternatively, the separate head/neck support section can be configured to fit loosely into the base support section. Further, the separate head/neck support section can have a top surface and a bottom surface and is of sufficient depth to mate snugly into the receptacle cutout of the base support section. In some embodiments, the head/neck support can be oval or generally round in shape. Additionally or alternatively, the head/neck support can be oval with one side being straight or one side being curved but with a differing radius from the other sides; the straight or curved part facing the front of the apparatus and having the neck support surface. The top surface of the separate head/neck support section can have a neck support for supporting the neck and a head support surface which slopes downward from the neck support towards the head end and towards the center of said head supporting surface. The back and sides of head/neck support section can be round or elliptical in shape where the sides of the head support surface slope downward and away from its edges towards the center of the head support section; while the front of the removable head/neck support section may be straight or curved with the head support surface sloping downward and away towards the center of this surface.

The front sides of the separate head/neck support section can include a front left neck supporting surface which slopes downwardly towards an occipital connecting line and a front right neck supporting surface which slopes downwardly towards an occipital connecting line both together creating a raised neck supporting surface with the middle of the neck supporting surface being lower than the outside portions of the neck supporting surface. The occipital connecting line can be a putative line that both bisects the midpoint of the neck support surface and the user's occiput when the user's head is positioned in the pillow. Head and neck support surfaces and front neck support surface can be dimensioned to align the orpharyngeal, the laryngeal and tracheal axes of the human upper airway into the sniff position in which the user's Occipito-Atlanto-Axial joint is adjusted to between about 5° and 30° of extension.

The base support section can be generally polygonal in shape, while the separate head/neck support section may be generally oval in shape. The raised neck support surface on the front side of the separate head/neck support section can have a generally cylindrical shape and may extend from the front left side of the head receiving surface to the right side of the head receiving surface (and vice versa) with the occipital connecting line being lower than the highest point of the left or right side of the raised neck supporting section.

The relative size of the supporting surfaces of the separate head/neck section can be varied in width, height, and/or depth thus accommodating various user head morphologies. Further, these various head/neck support sections (with varying head and neck support surface dimensions) can be fitted into a singular sized neck base support section greatly simplifying inventory requirements and reducing costs. For clarity of meaning for this embodiment it is clear that separate head/neck sections sized to accommodate widely diverse user head and neck sizes can be shaped to fit into a single sized support base section.

The base support section can have a ramped surface that slopes up and away from the front edge of the pillow at an angle of between about 20° and about 45° relative to the plane of the support surface, the angle being sufficient to elevate the neck/back and reduce the risk of acid reflux in users. The horizontal length of the ramp surface, from front edge of ramp to a plane at the front edge of the removable head/neck supporting surface, which is parallel to the support surface, can be between about 10-14 inches in length, which is sufficient to support a user's back and shoulders. In some embodiments, the head/neck support surface is not removable but is molded into the pillow.

Both the base support section and the head supporting sections can be constructed of non-allergenic materials such as EVA, urethane foam, latex foam or memory foam and may be shaped or molded. In the preferred embodiment the distance between neck supporting surface at the occiput connecting line and the bottom of the head supporting surface may be approximately about 2-6 inches and may vary by the size desired to fit the morphology of the user.

Additional features and advantages of the invention will be made apparent from the following detailed description of illustrative embodiments that proceeds with reference to the accompanying drawings.

The accompanying drawings, which are incorporated herein and form part of the specifications, illustrate various embodiments of a pillow for facilitating the supine sniff position, facilitating airway management, and reducing the complexity and cost of sizing such a pillow to a wide range of patient morphologies. Together with the descriptions the figures further serve to explain the principles of the pillow described herein and thereby enable a person skilled in the applicable arts to make the apparatus.

DETAILED DESCRIPTION

Figure 1G:
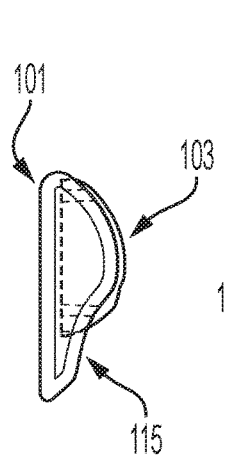
FIG. 1A, FIG. 1B, FIG. 1C, FIG. 1D, FIG. 1E, FIG. 1F, and FIG. 1G provide views of a pillow according to embodiments disclosed herein.

Reference will be made in detail to embodiments of the present invention with reference to the accompanying figures, in which like reference numerals will indicate like elements. While specific configurations are discussed it should be noted that this is for illustrative purposes.

The present disclosure relates to a pillow for aligning the oropharyngeal, laryngeal, and tracheal axes and the extension of the Occipito-Atlanto-Axial joint, together with flexion of the lower cervical spine for airway management with the user in the supine position while providing a convenient and cost-effective way to provide differing sizes of pillows to accommodate widely varying patient morphologies. Airway management can involve adjusting the patient head and neck for improved ventilation and respiration. By improving the position of a user's head and neck, the user can experience improved sleep, rest, oxygenation and ventilation and avoid airway obstruction and airflow turbulence that may result, for example, in snoring.

Various terms are used herein in accordance with their ordinary meanings. The term "about" as used herein denotes a variation of at most 10% around a numerical value. A substantial alignment of oropharyngeal, laryngeal, and tracheal axes as used herein means that an angle formed between any two of these axes is in a range of 0° and 30° with the Occipito-Atlanto-Axial joint having an angle of between 5° and 30° when a user's head and neck are positioned in the apparatus.

With reference to FIGS. 1A, 1B, 1C, 1C, 1D, 1E, and 1F, a pillow 100 according to one embodiment is disclosed, which allows alignment of the user's head and neck into the sniff position with a removable and replaceable head/neck section that can be fitted into a receptacle cut-out in a base support section of the pillow.

The removable head neck section 103 of the pillow 100 can be made to varying sizes for accommodating many users' neck and head sizes. The removable head section fits into receptacle cut-out 105 in the base support section 101.

Figure 1A:
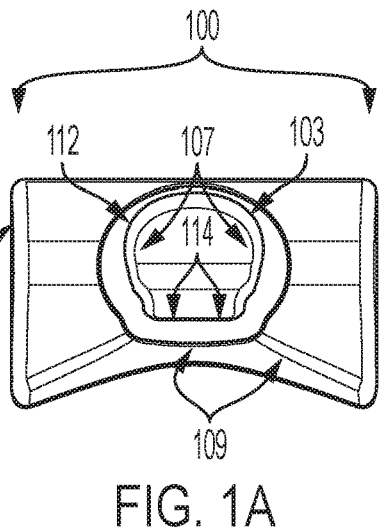
Figure 1C:
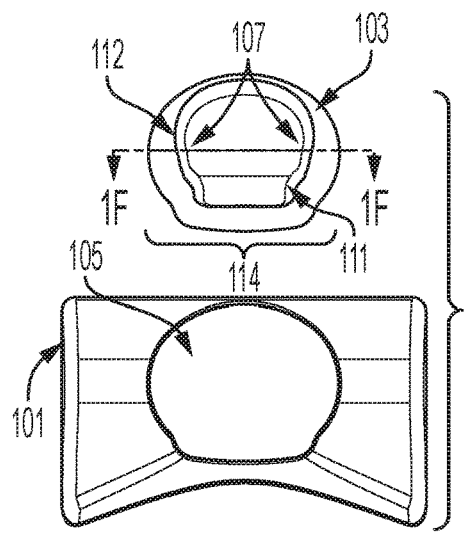
Figure 1B:
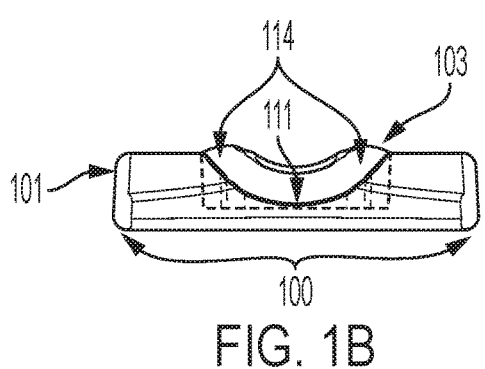

With reference to FIGS. 1A, 1B, 1C, and 1D, one embodiment of pillow 100 can include base support section 101 resting on a support surface (not shown) with shoulder cut out 109 and having removable head/neck support section 103 resting in a receptacle cut-out in the base support section 101 (not shown). Removable head/neck support section 103 has head support surface 107 and front neck support ridge 114 that together help position the user's airways into the sniff position. Base support section 101 and removable head/neck support 103 section can be made of various materials including polyurethane foam, EVA, latex foam, memory foam or other similar materials. The base support section 101 and removable head/neck support section 103 can be made of differing densities to allow firmer support for the base section and a softer cushion for the head/neck support section. Both sections can be molded, or cut, from foam or similar materials. Shoulder cut out 109 has an inclined ramp 115, which can be seen in FIG. 1G and is described below in FIGS. 3A, 3B and 3C. FIG. 1B, depicts a front view of one embodiment of pillow 100 that includes base support section 101 with occipital connecting line 111 bisecting front neck support ridge 114 of removable head/neck support section 103.

FIG. 1C depicts a top view of one embodiment of pillow 100 with removable head/neck support section 103 detached from support base section 101. Receptacle cut-out 105 can be sized to allow separate head/neck support section 103 to fit snugly into base support section 101. Removable head/neck support section 103 can have head support surface 107. The head support surface 107 can slope downward and away from edges of removable head/neck support section 103. Occiput connecting line 111 can bisect front neck support ridge 114 of removable head/neck support section 103 and along with head support surface 107 positions the user's head in the sniff position whereby the oropharyngeal, laryngeal, and tracheal axes are aligned and the Occipito-Atlanto-Axial joint extended between 5° and 30°.

Figure 1D:
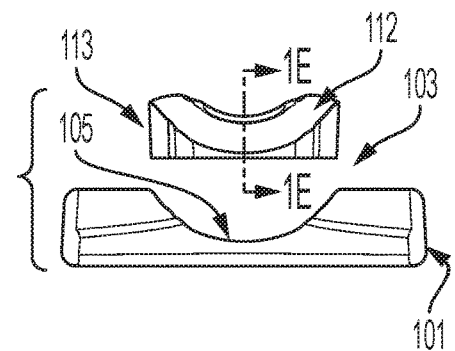

FIGS. 1B, 1D depict a front view of one embodiment of the pillow 100 with removable head/neck support section 103 detached from support base section 101. Removable head/neck support section 103 with front neck support ridge 114 and a fit portion 113 which is shaped, and sized, to fit into receptacle cut-out 105 in base support section 101 of this embodiment.

Figure 1E:
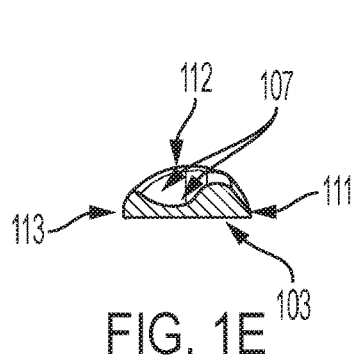

FIG. 1E depicts details and a sectional view of removable head/neck support section 103 along axis A-A from FIG. 1D. Removable head/neck support section 103 can have head support surface 107 which slopes downward and away from its outward edges and towards the user's head. Fit portion 113 can be shaped and sized to fit into receptacle cut-out 105 (shown in FIG. 1C and FIG. 1D). Front neck support ridge 114 and occiput connecting line 111 can work together with head support surface 107 in aligning the user's airways into the sniff position. It can be seen that the depth and size of head support surface 107 and the depth of the neck support at occiput connecting line 111 relative to the outer edges of neck support ridge 114 as well as the size of neck support ridge 114 can be varied. By varying the dimensions of these features, it can be seen that these resulting differing sizes of removable head/neck support sections can be made to fit many user morphologies.

Figure 1F:
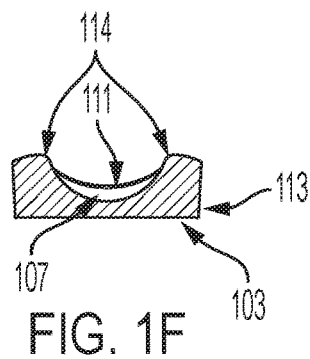

FIG. 1F depicts details and a sectional view of removable head/neck support section 103 along axis B-B from FIG. 1C. Removable head/neck support section 103 can have head support surface 107 which slopes downward and away from the edges of said surface and towards the user's head. Front neck support ridge 114 can be at front side of head support surface 107. Occipital connecting line 111 can bisect front neck support ridge 114 and can define the lowest point on front neck support ridge 114.

FIG. 1G depicts a side view of pillow 100 with support base section 101, removable head/neck support section 103, and sloping surface 115 of shoulder cut out 109 (shown in FIG. 1A). Sloping surface 115 of shoulder cut out 109, depicted in FIG. 1A, facilitates inspiration by taking the center of gravity of the weight of the chest and abdomen away from the lung/diaphragm functional unit as well as decreasing the problem of gastrointestinal reflux.

Figure 2A:
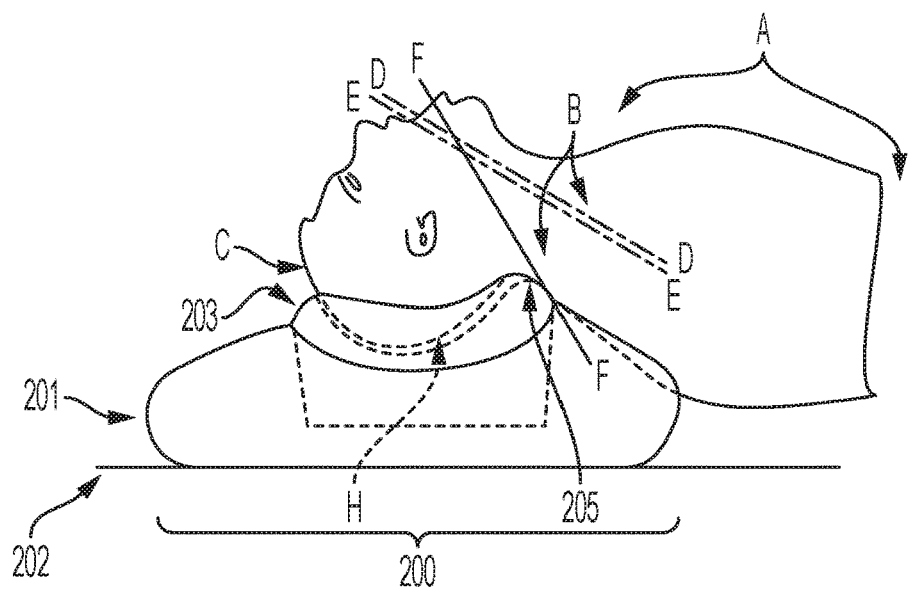
FIG. 2A provides side view of the pillow 200 with user's head in pillow along with details of the present invention, FIG. 2B and FIG. 2C provide sectional views of pillow 200.
Figure 2B:
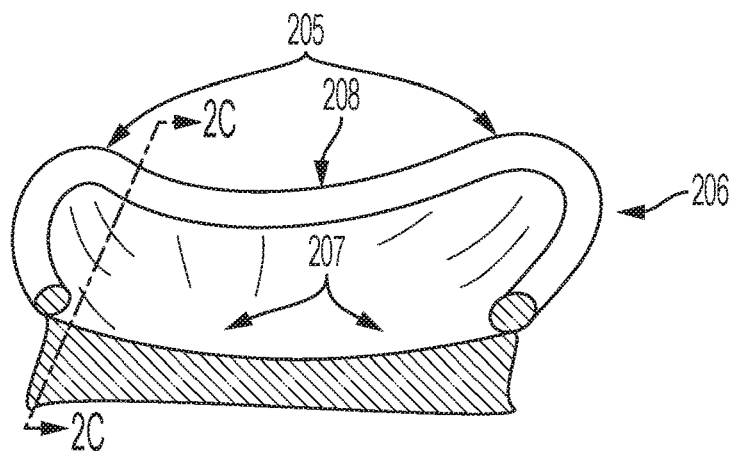
Figure 2C:
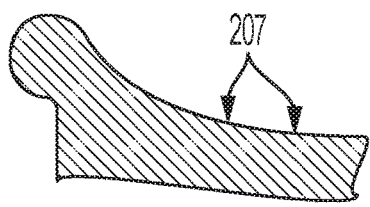

FIG. 2A, FIG. 2B, and FIG. 2C depict an embodiment of the pillow 200, in use during which support base 201 rests on a support surface 202. User A is shown with head positioned in pillow 200, user's neck B is positioned on front neck support ridge 205 with occipital contact line 208 bisecting the center of front neck support ridge 205; the back sides of head C are supported on surface 207 which slopes downward and away from front neck support surface 204. Axis D-D represents the oropharyngeal axis, axis E-E represents the laryngeal axis, and axis F-F represents the tracheal axis. Due to the relationship, and slope of head support surface 207, to front neck support ridge 205 lateral movement of the user's head is facilitated and automatic positioning of the user into the sniff position occurs. As a result of the orientation of surfaces 207, 204 and 208 axes E-E, T-T and L-L are aligned and into the sniff position. Because head support surface 207 slopes downwardly from front neck ridge 205 the Occipito-Atlanto-Axial joint is extended upwards and head C is angled downwardly towards the support surface to align head C and neck B of user into the sniff position aligning airways E-W, T-T and L-L. When user head C is positioned as shown the Occiput H of the user's skull is in line with Occipital connecting line 208, which bisects front neck support ridge 208 with the head C contacting sloping support surface 207 that keeps the user in the sniff position.

Figure 3A:
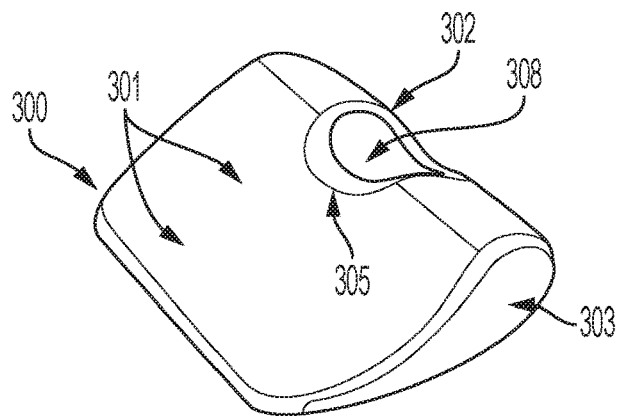
FIG. 3A provides a perspective view of pillow 300 with sloping ramp while FIGS. 3B and 3D provide top views of pillow 300 while FIG. 3C provides a side view.

FIGS. 3A, 3B, 3C, and 3D depict another embodiment of the invention, pillow 300. FIG. 3A provides a perspective view of pillow 300 with sloping ramp 301, head receiving area 308, and removable head/neck support section 302 and support base section 303. It is understood that in other embodiments the head neck support area may be molded into base 303 and may not be removable and/or replaceable. Head/Neck receiving area has front neck support 305 that provides support and positioning for user's neck and is sized for such. Head receiving area 308 slopes down and away from outer edges and towards the center of removable head/neck support section; this slope positioning the head properly, along with front neck support 305, to align the user into the sniff position.

Figure 3B:
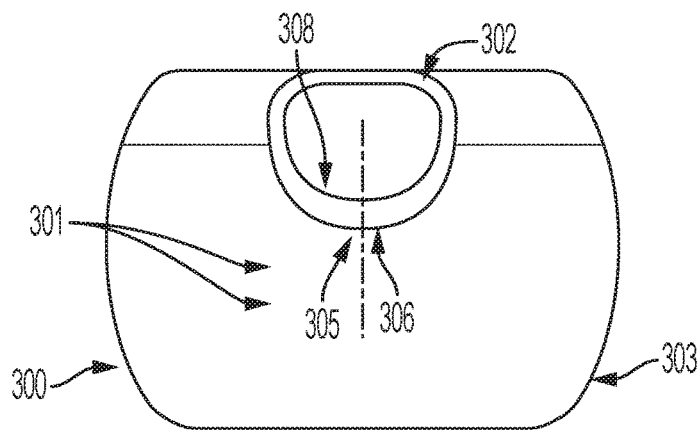
Figure 3C:
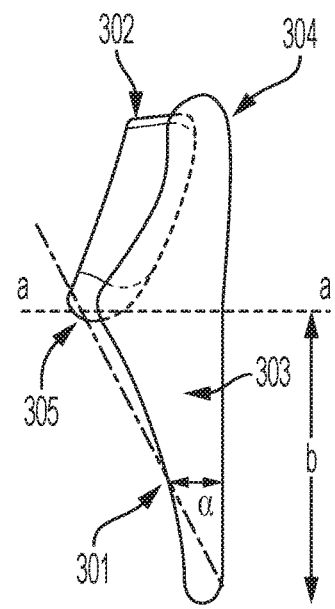
Figure 3D:
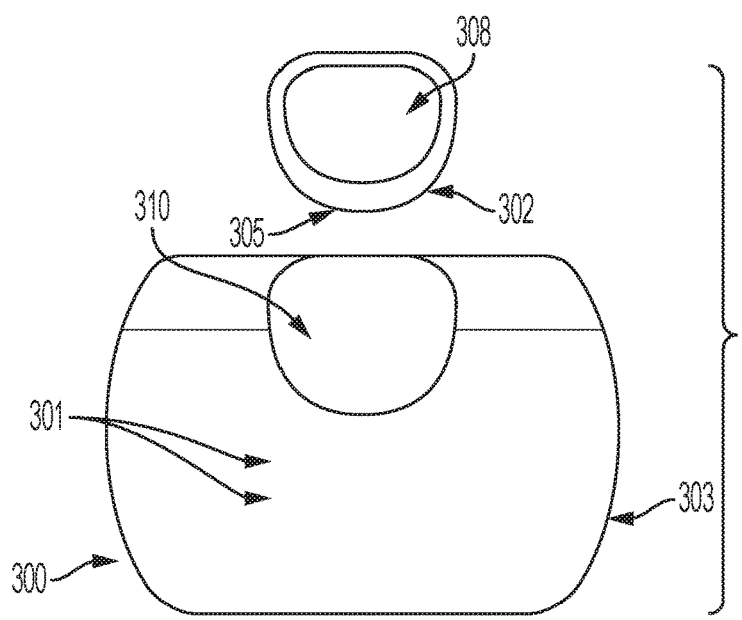

FIG. 3B provides a top view of pillow 300 with sloping ramp 301, removable head/neck support area 303 (which in some embodiments may not be removable and may be molded into support base section). Base support section 303 has sloped ramp 301, which elevates users' backs and shoulders. Occipital contact line bisects front neck support surface 306 and removable head/neck support 302. Removable head/neck support has front neck support surface 305 and head receiving area 308. FIG. 3D depicts view of pillow 300, with base support section 303 with ramp 301 sloping up and away from support surface (not shown) and towards removable head/neck support section 302. In this embodiment head neck support section is removable/replaceable; in others it is molded into base section 303. Head/neck support section 302 is shown pulled out of receptacle cut out 310 in base support section 303. Head neck support section fits snugly into receptacle cutout 310. FIG. 3C is a side view of pillow 300 with base section 303 resting on support surface 304 with sloping ramp 301 and removable head/neck support 302. In this embodiment head/neck support 302 is removable and replaceable, but in other embodiments it is molded into base 303. Slope ramp is a compound curve with angle α shown as the angle between support surface 304 and sloping ramp 301 with angle α varying between about 20°-30°, such an angle being sufficient to elevate the chest and back of a user to reduce the occurrence/risk of acid reflux.

A pillow according to the present teachings can be fabricated in a variety of different sizes. For example, a pillow based on the present teachings can be made on a small scale for pediatric/adolescent population with sleep disordered breathing.

What is claimed is:

1. A support apparatus for supporting and maintaining the head and neck of a user in the supine sniff position in which the Occipito-Atlanto-Axial joint is extended upwards and the head is angled downward to achieve alignment of the airway axes, comprising:
a base section comprising:
opposing left and right sides, a back side, a front side, a bottom surface and a cutout for receiving lower back and shoulders the base section comprising a receptacle for receiving a removable and replaceable head/neck support section wherein:
the removable and replaceable head/neck support section comprises an appendage for fitting snugly into the receptacle; and
the removable head/neck support section comprises:
a neck supporting surface at a neck end thereof for supporting the neck; and
a head supporting surface for supporting the head, the head supporting surface including a central surface that slopes downwards and away from the neck supporting surface and downwards and away from outer edges of the head supporting surface; and
the removable head/neck support section is dimensioned to automatically align and maintain substantial alignment of the oropharyngeal, laryngeal, and tracheal axes;
two or more top sections each with one or more sections comprising an extension or appendage configured to fit snugly into a corresponding cutout in the base section; each top section being interchangable for other section and being configured for to being fitted into the base section;
two or more top sections each with a neck supporting surface for supporting the neck, the neck support being positioned at the neck end of the top section; each top section being interchangable for the other and configured for being fitted into the base section;
two or more top sections with differing sized head support surfaces for supporting the head, this head supporting surface including a central surface that slopes down and away from the neck supporting surface and down and away from the outer the edges of the head supporting surface; and
two or more top sections with a head support and neck support being dimensioned to automatically align and maintain substantial alignment of the orpharyngeal, laryngeal, and tracheal axes, substantial alignment being defined as between about 0° and about 30° with the Occipito-Atlanto-Axial joint having an angle of extension between about 5° and about 30° when user's head and neck are positioned in the apparatus.

2. The apparatus set forth in claim 1, wherein the base support section is substantially rectilinear in shape.

3. The apparatus set forth in claim 1, wherein the neck supporting surface in the removable neck/head support section is generally cylindrical or rounded.

4. The apparatus set forth in claim 1, wherein the neck supporting surface in the removable neck/head support section is generally cylindrical or oval in shape with a maximum diameter of at least 0.25 inches.

5. The apparatus set forth in claim 1, wherein the middle of the neck supporting surface in the removable neck/head support section is lower than the ends of the neck supporting section by at least 0.125 inches.

6. The apparatus set forth in claim 1, wherein the support apparatus is formed of urethane foam that is molded.

7. The apparatus set forth in claim 1, wherein the urethane foam material is cut or carved to form the apparatus.

8. The apparatus set forth in claim 1, wherein the highest edge of the neck supporting surface is between 0.5 and 4 inches higher than lowest point on the head supporting surface.

9. A support apparatus for supporting and maintaining the head and neck of a user in the supine sniff position in which the Occipito-Atlanto-Axial joint is extended upwards and the head is angled downward to achieve alignment of the airway axes, comprising:
a base section comprising:
opposing left and right sides, a back side, a front side, a bottom surface and a cutout for receiving lower back and shoulders, the cutout being configured to receive and fit a second section of the apparatus, and the base section comprising a receptacle for receiving a removable and replaceable head/neck support section, wherein:
the removable and replaceable head/neck support section comprises an appendage for fitting snugly into the receptacle; and
the removable head/neck support section comprises:
a neck supporting surface at a neck end thereof for supporting the neck; and
a head supporting surface for supporting the head, the head supporting surface including a central surface that slopes downwards and away from the neck supporting surface and downwards and away from outer edges of the head supporting surface; and
the removable head/neck support section is dimensioned to automatically align and maintain substantial alignment of the oropharyngeal, laryngeal, and tracheal axes, and the apparatus further comprising:
two or more top sections each with one or more sections comprising an extension or appendage configured to fit snugly into a corresponding cutout in the base section; each top section being interchangable for the other and configured to be fitted into the base section;
two or more top sections each with a differing size neck supporting surfaces for supporting the neck, the neck support being positioned at the neck end of the top section; each top section being interchangable for the other and configured to be fitted into the base section;
two or more top sections with a head support for supporting the head, this the head supporting surface including a central surface configured to slope down and away from the neck supporting surface and down and away from the outer the edges of the head supporting surface; and
two or more top sections with a head support and neck support being dimensioned to automatically align and maintain substantial alignment of the orpharyngeal, laryngeal, and tracheal axes, substantial alignment being defined as between about 0° and about 30° with the Occipito-Atlanto-Axial joint having an angle of between about 5° and about 30° when user's head and neck are positioned in the apparatus.

10. A support apparatus for supporting and maintaining the head and neck of a user in the supine sniff position in which the Occipito-Atlanto-Axial joint is extended upwards and the head is angled downward to achieve alignment of the airway axes, comprising:

a base section comprising:
opposing left and right sides, a back side, a front side, a bottom surface and a cutout for receiving lower back and shoulders, the cutout being configured to receive and fit a second section of the apparatus, and the base section comprising a receptacle for receiving a removable and replaceable head/neck support section, wherein:
the removable and replaceable head/neck support section comprises an appendage for fitting snugly into the receptacle; and
the removable head/neck support section comprises:
a neck supporting surface at a neck end thereof for supporting the neck; and
a head supporting surface for supporting the head, the head supporting surface including a central surface that slopes downwards and away from the neck supporting surface and downwards and away from outer edges of the head supporting surface; and
the removable head/neck support section is dimensioned to automatically align and maintain substantial alignment of the oropharyngeal, laryngeal, and tracheal axes, and the apparatus further comprising:

two or more top sections each with one or more sections comprising an extension or appendage that will fit snugly into a corresponding cutout in the base section; each top section being able to be interchanged for the other and to able to be fitted into the base sections;

two or more top sections each with a differing size neck supporting surface for supporting the neck, the neck support being positioned at the neck end of the top section; each top section being able to be interchanged for the other and to able to be fitted into the base section;

two or more top section with differing sized head support surfaces for supporting the head, this head supporting surface including a central surface that slopes down and away from the neck supporting surface and down and away from the outer the edges of the head supporting surface;

two or more top sections with a head support and neck support being dimensioned to automatically align and maintain substantial alignment of the orpharyngeal, laryngeal, and tracheal axes, substantial alignment being defined as between about 0° and about 30° with the Occipito-Atlanto-Axial joint having an angle of between about 5° and about 30° when users head and neck are positioned in the apparatus.

* * * * *